United States Patent [19]

Estrada, Jr. et al.

[11] 4,145,922
[45] Mar. 27, 1979

[54] THERMAL POWER MEASUREMENT APPARATUS

[75] Inventors: Herbert Estrada, Jr., Annapolis, Md.; Dwight H. Harrison, Vienna; Laurence E. Demick, Falls Church, both of Va.

[73] Assignee: Westinghouse Electric Corp., Pittsburgh, Pa.

[21] Appl. No.: 748,258

[22] Filed: Dec. 6, 1976

[51] Int. Cl.² .............................................. G01K 17/06
[52] U.S. Cl. ..................................... 73/193 R; 73/597
[58] Field of Search ................. 73/112, 193 R, 194 A, 73/560, 339 A, 344

[56] References Cited

U.S. PATENT DOCUMENTS

| | | | |
|---|---|---|---|
| 1,948,234 | 2/1934 | Johnson | 73/193 R X |
| 2,911,826 | 11/1959 | Kritz | 73/194 A |
| 3,564,912 | 2/1971 | Malone et al. | 73/194 A X |
| 3,575,050 | 4/1971 | Lynnworth | 73/67.5 R X |
| 3,636,754 | 1/1972 | Lynnworth et al. | 73/194 A |

OTHER PUBLICATIONS

Lynnworth-IEEE Transactions on Sonics and Ultrasonics-vol. 50-22, No. 2, Mar. 1975, pp. 71, 81.

Primary Examiner—Charles A. Ruehl
Attorney, Agent, or Firm—D. Schron

[57] ABSTRACT

Measuring apparatus for a system which includes a heat source such as a nuclear reactor and a utilization means such as a steam generator connected by first and second fluid conveying ducts in a closed circulation loop. A multi-path acoustic flowmeter in one leg of the loop obtains an indication of volumetric flow rate as well as an indication of the speed of sound in that leg. A multi-path acoustic measuring apparatus in the other leg obtains an indication of the speed of sound in that leg and electronic circuitry is provided for modifying the indications and combining them to obtain total thermal power.

19 Claims, 11 Drawing Figures

DENSITY VS. SOUND VELOCITY

ENTHALPY VS. SOUND VELOCITY

THERMAL POWER MEASUREMENT APPARATUS

BACKGROUND OF THE INVENTION

1. Field of the Invention

Thermal power measurement.

2. Description of the Prior Art

A need exists for obtaining an absolute measurement of the thermal power generation or consumption of any system using flowing fluid for heat transport. For example, in a nuclear reactor power plant, a typical arrangement includes a nuclear reactor and a steam generator with circulating fluid being provided from the reactor to the generator by way of an outlet leg (hot leg) with fluid being returned back to the reactor from the generator by way of an inlet leg (cold leg) in a closed loop known as the primary loop. The steam generator in turn may be connected to a power generation device such as a turbine in another closed loop known as the secondary loop.

In the nuclear plant, the thermal power of the primary loop is the power which the nuclear reactor is producing and is measured in thermal energy per unit of time. The thermal power of the secondary loop is the power that the steam generator provides and should be equal to the thermal power of the primary loop. Nuclear regulations require that the plant be operated at certain prescribed ratings and knowledge of thermal power would insure conformance with the requirement. In addition, measurements are needed to account for fuel burnup and to calibrate power control systems. Of equal importance is the fact that thermal power measurement provides an indication of the plant efficiency.

In addition to nuclear plants, thermal power knowledge is also desirable in fossil fuel power plants as well as other closed loop systems such as heat exchangers and chemical reactors. There is however, no available system which will provide a thermal power measurement to a high degree of accuracy, such as one percent or less. For thermal power measurement the flow rate of the circulating fluid must be known as well as other of its properties, such as density and enthalpy, which is a quantity established by arbitrary definition and is the sum of the internal energy and potential energy of the fluid. Other terms such as total heat, heat content, and thermal potential have been used; however, the designation enthalpy is preferred.

In presently proposed systems, measurement of fluid pressure and temperature are required. The pressure of the circulating fluid in such systems typically may be in the order of thousands of psi and the variation of pressure during operation is relatively small and insignificant. Accordingly, no difficulty is encountered in the obtaining of pressure measurements. With respect to temperature measurements, however, wherein the circulating fluid is a liquid, temperature gradients exist across the fluid in the duct and a single temperature measurement such as obtained by a thermocouple near the fluid-duct interface, may not accurately represent the average temperature of the fluid in the duct passing that thermocouple. Multiple thermocouples may be positioned around the duct, however, the same problem exists. To provide a fair indication of the temperature across the fluid a plurality of thermocouples would have to be positioned at various points within the duct; however this is objectional since it presents an obstruction to fluid flow, and if a thermocouple or thermal measuring device should break loose, it could cause significant damage.

SUMMARY OF THE INVENTION

For fluid systems such as described, the thermal power is given by the product of the mass flow rate and the change in enthalpy of the fluid. For the vast majority of fluids used in such systems the sensitivity of enthalpy and density to changes in pressure is negligible and in the present invention, pressure measurements may be foregone and sound velocity used to establish fluid enthalpy and density.

The apparatus includes an acoustic meter preferably having a plurality of acoustic measuring paths traversing the fluid, to obtain an indication of volumetric flow rate of the fluid in one of the legs of the loop. This same acoustic meter may be modified so as to obtain, acoustically, sound velocity through the fluid in that leg. A similar but simpler multi-path acoustic meter may be placed in the other leg to obtain an indication of sound velocity and electronic circuit means are provided for modifying and combining the indications to obtain a thermal power measurement.

DESCRIPTION OF THE PREFERRED EMBODIMENT

Figure 1:
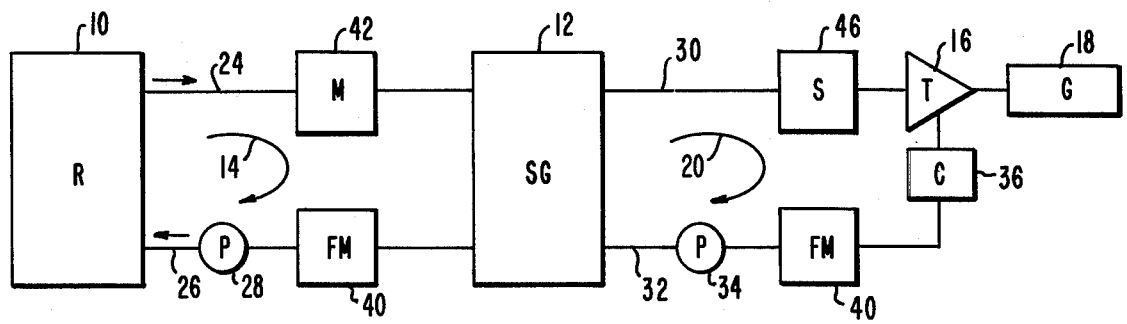
FIG. 1 is a block diagram of a flowing fluid heat transport system.

Referring now to FIG. 1, there is illustrated a representative system which uses flowing fluid for heat transport. The system includes a heat source 10 and a load 12 with fluid circulating around a loop 14. By way of example, the invention will be described with respect to a nuclear power plant with the heat source 10 being a pressurized water nuclear reactor. Load 12 is a steam generator which in itself will be a heat source for a load 16 in the form of a turbine which drives a generator 18 and with fluid circulating around loop 20. The loop 14 is commonly known as the primary loop and loop 20 is known as the secondary loop.

Circulating fluid is conducted from reactor 10 to steam generator 12 by way of the outlet or hot leg 24, while the fluid is returned from steam generator 12 back to reactor 10 by way of the inlet or cold leg 26 which also includes a fluid circulating pump 28.

On the secondary side, circulating fluid, steam, is provided to turbine 16 by way of the outlet or hot leg 30 from the steam generator 12 and fluid in the form of water is returned to steam generator 12 by means of inlet or cold leg 32 which includes a circulating pump 34 and a condenser 36.

In the present invention, a flowmeter, and preferably a multi-path acoustic flowmeter is positioned in one of the legs of a loop to obtain an indication of mass flow rate of the circulating fluid. Thus, by way of example, flowmeter 40 is positioned in the cold leg of primary loop 14. The thermal power of the reactor is calculated by additionally obtaining an indication of the enthalpy difference between the fluid in the hot and cold legs and this is accomplished by utilizing acoustic meters and preferably milti-path acoustic meters to obtain the sound velocity in both the hot and cold legs 24 and 26. Accordingly, a multi-path acoustic meter 42 is positioned in the hot leg 24 and if desired, an identical meter can be positioned in the cold leg 26. To save equipment and installation costs, however, flowmeter 40 may itself be modified to additionally provide the sound velocity indication for the cold leg.

The secondary side of the system also includes a multi-path acoustic flowmeter 40 for obtaining volumetric flow rate and sound velocity in the cold leg 32 and a sensor 46 may be placed in the hot or steam leg 30 for obtaining certain parameters, as will be explained.

A multi-path acoustic flowmeter has been developed which provides a highly accurate indication of volumetric flow rate. The system utilizes pairs of opposed transducers installed at the boundary of a fluid conveyance so as to form parallel acoustic paths accurately positioned relative to the boundary in accordance with a numerical integration technique such as the Gaussian technique. The transducers simultaneously project an acoustic pulse toward an opposing transducer and the time of flight of the upstream travelling and downstream travelling pulse in each path to the opposing transducer is utilized with proper Gaussian weighting factors to provide an indication of volumetric flow rate. The Gaussian technique together with its positioning and weighting factors, is described in U.S. Pat. No. 3,564,912, and variations thereof in U.S. Pat. No. 3,940,985, and application Ser. No. 599,209 filed July 25, 1975, now U.S. Pat. No. 4,024,760, all of which are herein incorporated by reference.

Figure 2:
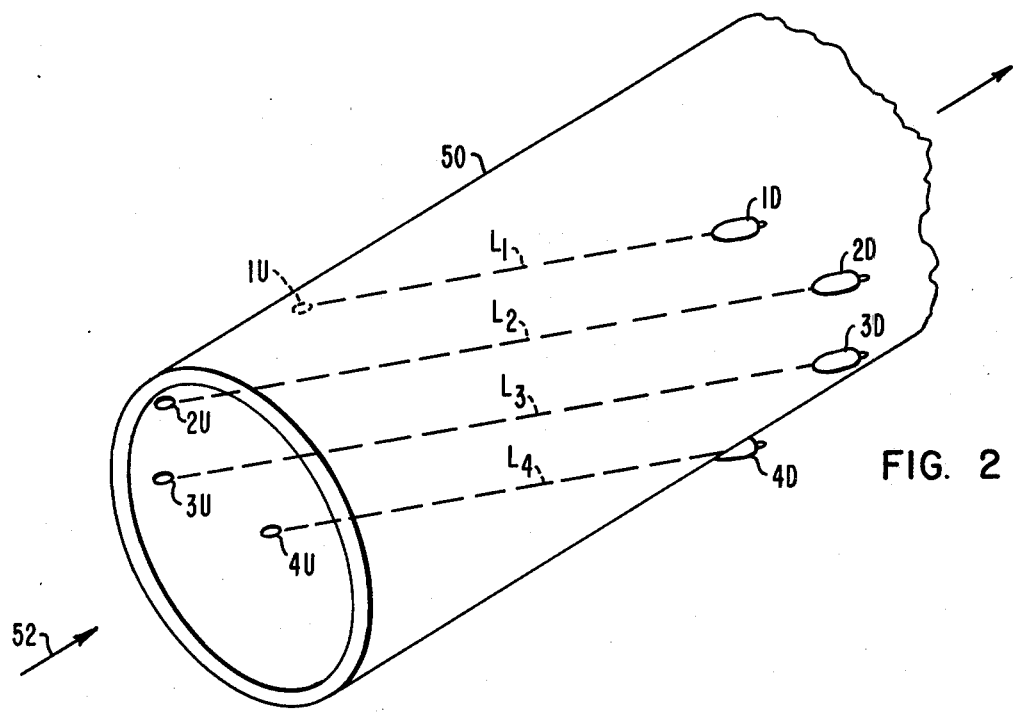
FIG. 2 illustrates a portion of a fluid conveying duct with a multi-path acoustic transducer placement.

In FIG. 2 there is illustrated a section of duct 50 which, in the present example, is a portion of the cold leg 26 which conducts circulating fluid in an upstream to downstream direction as indicated by arrow 52. In the multi-path system, a plurality of pairs of transducers are provided with one transducer of each pair constituting an upstream transducer and the other a downstream transducer both in acoustic communication with the fluid in the duct, with the two defining an acoustic path between them.

For example, upstream transducer 1U in conjunction with its opposed downstream transducer 1D define an acoustic path between them of length $L_1$. The second pair of transducers 2U and 2D define a second path of length $L_2$. Opposed transducers 3U and 3Ddefine another acoustic path of length $L_3$ and transducers 4U and 4D define an acoustic path of length $L_4$. For the four-path system as shown, and for a circular duct, the transducers are generally positioned such that $L_1$ is equal to $L_4$ and $L_2$ is equal to $L_3$.

Figure 2A:
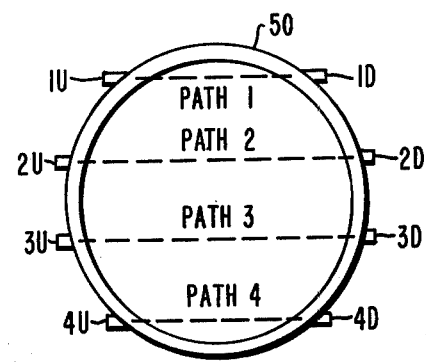
FIG. 2A is a view of FIG. 2 looking in along the central axis of the duct.

FIG. 2A is a view of the arrangement looking down the duct axis in the direction of fluid flow.

Due to the absence of protrusions in the hydraulic circuit, use of such arrangement minimizes the potential for mechanical failures of the measuring equipment which could damage other components of the circuit. Additionally such arrangement generates no pressure drop and the energy loss expended on the power measurement itself is nil.

Before proceeding the detailed description of the invention it would be beneficial to have an understanding of fluid flow measurements utilizing acoustic pulse travel times. In a single path system, volumetric flow rate may be determined by simultaneously energizing an upstream and downstream transducer and measuring the acoustic pulse downstream travel time and the acoustic pulse upstream travel time. If t1 is the downstream travel time and t2 the upstream travel time the volumetric flow rate Q may be determined by the relationship:

$$Q = K \frac{t2 - t1}{t1 t2} \quad (1)$$

where K is a constant dependent upon such factors as L, the path length between transducers, $\theta$, the angle that the path makes with respect to fluid flow, and conversion units. The difference in travel times of the oppositely directed acoustic pulses along the path is $\Delta t$ and $$\Delta t = t2 - t1 \quad (2)$$

Since $t2 = t1 + \Delta t$ $$Q = K \frac{\Delta t}{t1(t1 + \Delta t)} \quad (3)$$

Equation (3) may be implemented with the provision of two counters, one a t1 counter which is turned on at the time of the acoustic transmission and which is turned off when the downstream transducer receives the acoustic pulse. A second counter, a $\Delta t$ counter, is turned on when the downstream pulse is received and is turned off when the upstream pulse is received with the resulting count being indicative of the difference in travel times.

A much more accurate determination of volumetric flow rates may be obtained with the multi-path system utilizing numerical integration techniques such as the Gaussian technique where:

$$Q = \sum_{i=1}^{n} (W_i L_i^2 \tan\theta \frac{D}{2}) \frac{\Delta t_i}{t1_i(t1_i + \Delta t_i)} \quad (4)$$

The following additional definitions are used:
 Q is the volumetric flow rate
 D is the diameter of the duct
 n is the number of paths
 i is a particular path number
 $W_1$ is the Gaussian weighting factor for the $i^{th}$ path.

Power calculation is based upon the product of mass flow rate and change of enthalpy, and in the present example, has the form:

$$P = Q\rho (h_H - h_C) \quad (5)$$

With the flowmeter being positioned in the cold leg by way of example,

Q is the volumetric cold leg fluid flow in cubic feet per second $\rho$ is the average cold leg fluid denity in pounds per cubic feet $h_H$ is the average fluid enthalpy in the hot leg in BTU's per pound $h_C$ is the average fluid enthalpy in the cold leg in BTU's per pound Since $Q\rho$ is the mass flow rate and Q is provided by the flowmeter in accordance with equation (4), it is necessary to obtain the cold leg fluid density $\rho$. This is accomplished in the present invention by calculation of the cold leg fluid sound velocity $C_C$. For example, and with reference to FIG. 3, curve 54 represents the relationship between the circulating fluid density with respect to sound velocity through the fluid in the pressurized system where pressure variations are small. For example, in a typical system operated at thousands of psi, the pressure variation may typically be ±20 psi.

Figure 3:
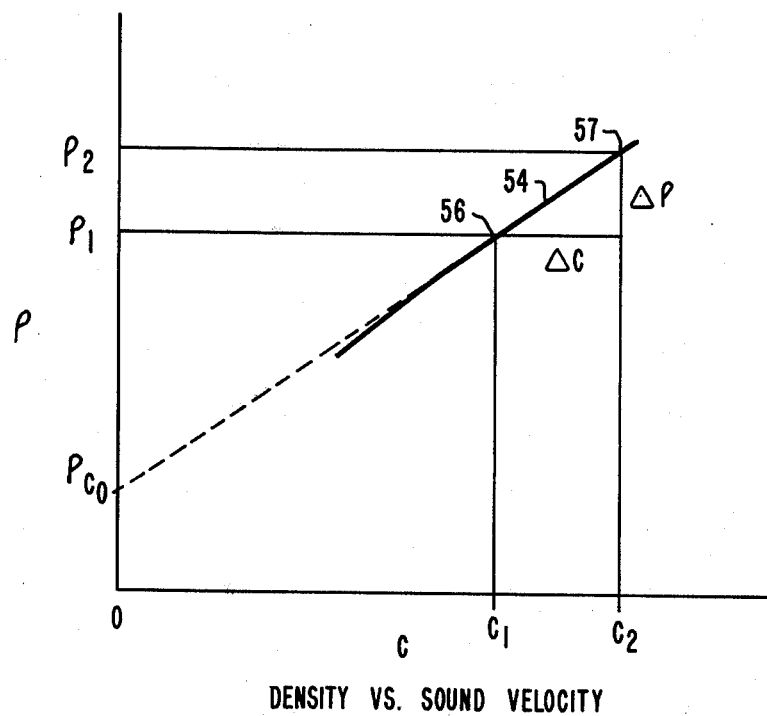
FIG. 3 is a curve of density versus sound velocity.

A typical operating range in FIG. 3 will be between points 56 and 57, point 56 representing a fluid density of $\rho_1$ with a sound velocity of $C_1$ and point 57 representing a fluid density of $\rho_2$ with a sound velocity of $C_2$. The operating curve between points 56 and 57 is essentially linear and an extrapolation of this linear portion intersects the $\rho$ axis where C equals 0 at a point $\rho_{C_0}$.

According to the formula for a straight line, $$y = mx + b \tag{6}$$

where m is the slope of the line and b is the intercept on the y axis. Applying this formula to the curve of FIG. 3

$$\rho = (\partial\rho/\partial C)_P \, C + \rho_{c_0} \tag{7}$$

where the term $(\partial\rho/\partial C)_P$ represents the slope (m) of the curve and is in the form of the derivative of a function with respect to one variable, all other variables, in this case, pressure, being treated as constants, as represented by the subscript P.

Thus, having Q and having $\rho$, mass flow rate $Q \times \rho$ may be obtained. For thermal power measurement, it is also necessary to obtain the enthalpy difference between the hot and cold legs and to this end reference is now made to FIG. 4 which is a curve of enthalpy versus sound velocity.

Curve 60 has a negative slope and the portion of the curve between point 62 and 63, representing an operating range is to a good approximation, linear, and the extrapolation of this linear portion intercepts the enthalpy axis at some value $h_{C_0}$.

Figure 6:
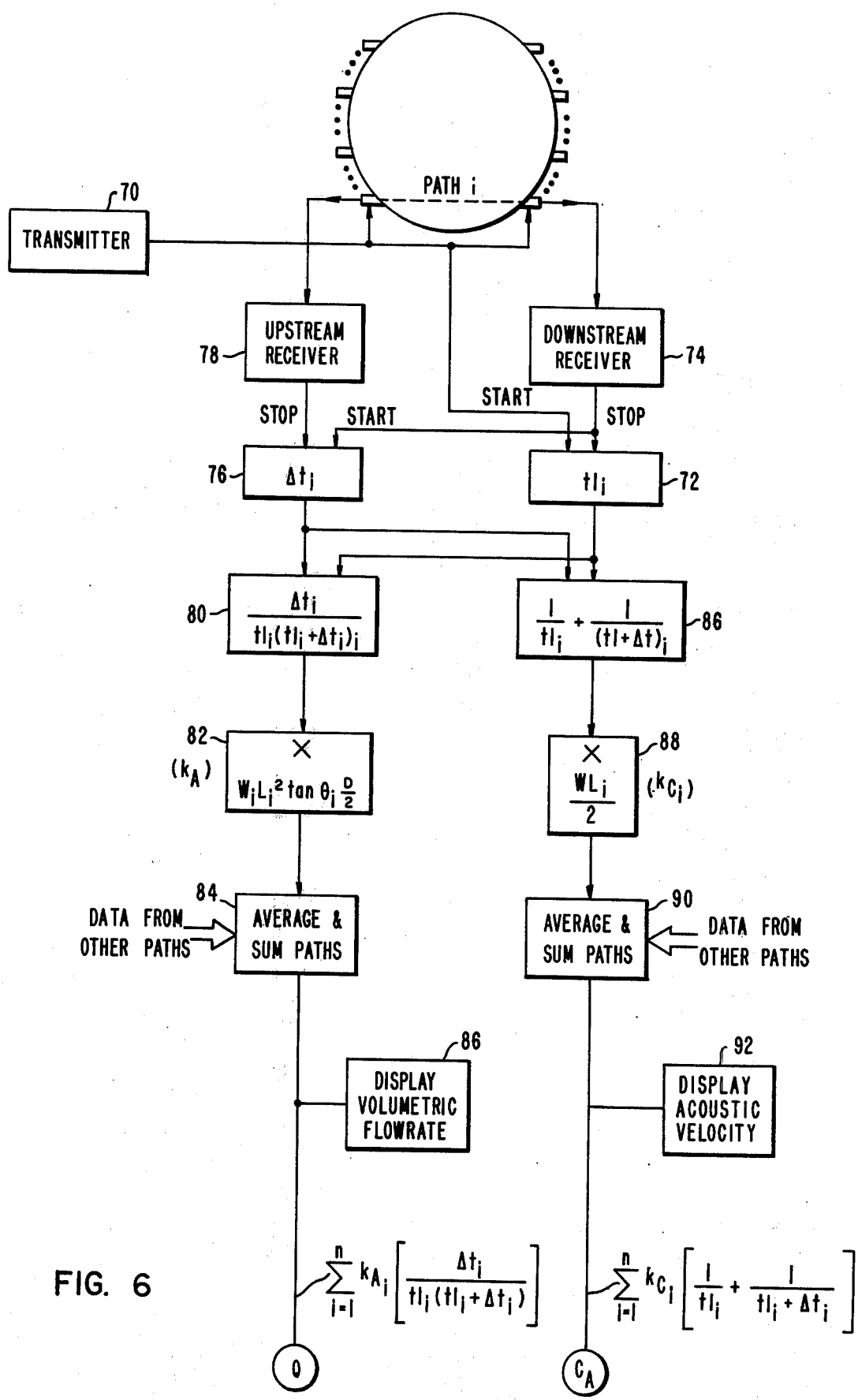
FIG. 6 is a block diagram of electronic circuitry for obtaining volumetric flow rate and sound velocity in one leg of the loop.

Assuming that point 62 represents the hot leg enthalpy and point 63 the cold leg enthalpy, from the straight line equation of FIG. 6

$$h_H = (\partial h/\partial C)_P \, C_H + h_{c_0} \tag{8}$$

and $$h_C = (\partial h/\partial C)_P \, C_C + h_{c_0} \tag{9}$$

Subtracting equation (9) from equation (8)

$$h_H - h_C = (\partial h/\partial C)_P \, [C_c] \tag{10}$$

Figure 4:
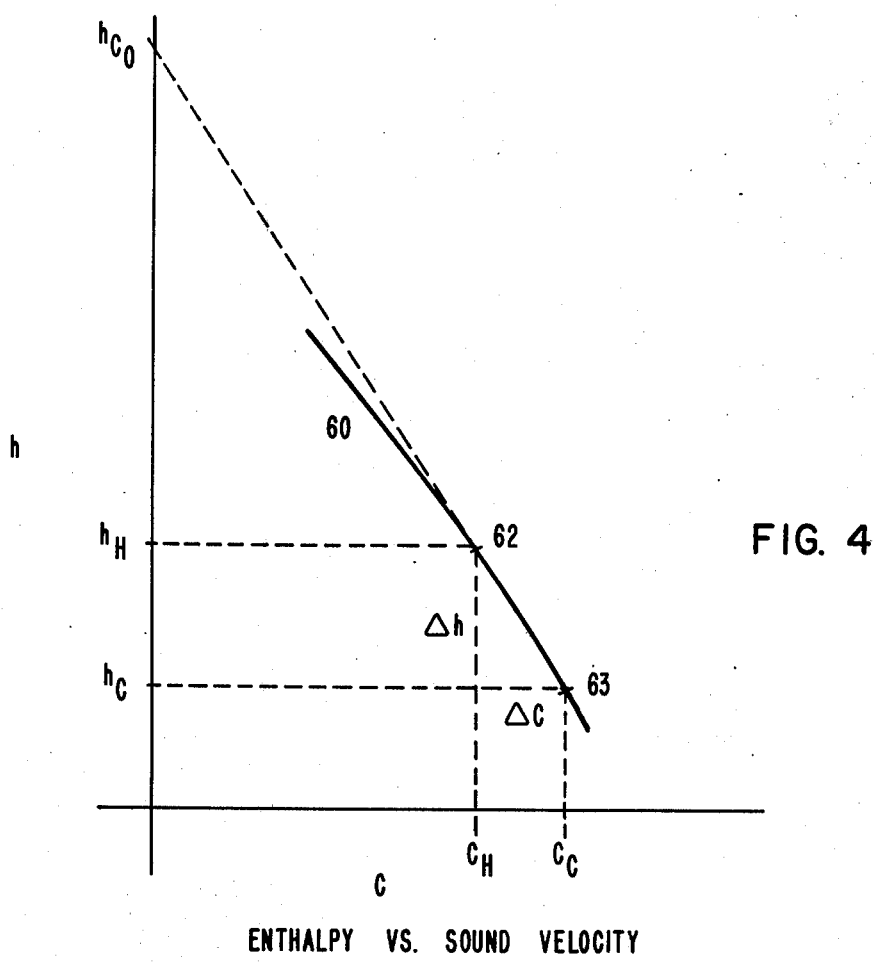
FIG. 4 is a curve of enthalpy versus sound velocity.

Accordingly, the enthalpy difference, needed for the power calculation, can be derived by obtaining an indication of the velocity of sound in the fluid in the hot leg ($C_H$) and the velocity of sound in the fluid in the cold leg ($C_C$) with $(\partial h/\partial C)_P$ being a constant equal to the slope of the curve of FIG. 4 within the operating range.

Considering for simplicity just a single path system, the time of flight of the acoustic pulse traveling downstream is $$t1 = L/(C + V) \tag{11}$$

and the time of flight of the acoustic pulse traveling in an opposite direction upstream is $$t2 = L/(C - V) \tag{12}$$

where V is the fluid velocity component along the path between the transducers and L is the path length between the transducers. Since $$1/t1 = (C + V)/L \tag{13}$$

and $$1/t2 = (C - V)/L \tag{14}$$

adding the two together results in:

$$\frac{1}{t1} + \frac{1}{t2} = \frac{C + V + C - V}{L} = \frac{2C}{L} \tag{15}$$

C therefore is $$C = \frac{L}{2}\left(\frac{1}{t1} + \frac{1}{t2}\right) \tag{16}$$

Since, from equation (2), t2 is equal to t1 + $\Delta t$ $$C = \frac{L}{2}\left(\frac{1}{t1} + \frac{1}{(t1 + \Delta t)}\right) \tag{17}$$

All the quantities of equation (17) are known or are provided by the flowmeter and accordingly the relationship may be used in a multi-path system, with proper Gaussian modification, to derive the sound velocity in the cold leg. If the acoustic paths are perpendicular to the flow direction then the acoustic pulses are unaffected by the velocity of the fluid. For example, with reference to FIG. 5, duct 68, representing in the present example a portion of the hot leg, includes a plurality of transducers T1 to T4 together with respective opposed transducers T1' to T4'. The acoustic paths between transducer pairs all lie in the same plane, which plane is perpendicular to the fluid flow direction as indicated by the arrow. A view of the arrangement looking in along the axis is illustrated in FIG. 5A.

Since the acoustic pulses are unaffected by the fluid velocity, $$t1 = t2 \tag{18}$$

and $$C = \frac{L}{2}\left(\frac{1}{t1} + \frac{1}{t1}\right) \tag{19}$$

$$C = \frac{L}{t1} \tag{20}$$

Figure 5:
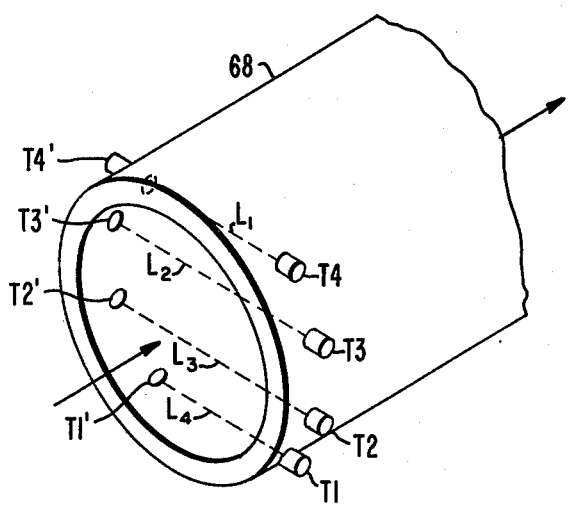
FIG. 5 illustrates a portion of a fluid conveying duct with a multi-path acoustic transducer placement for obtaining sound velocity in the duct.
Figure 5A:
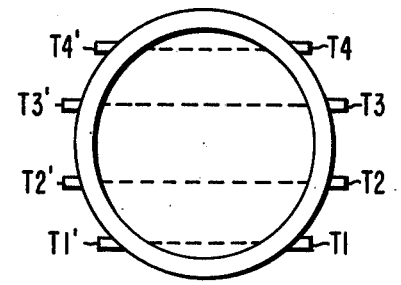
FIG. 5A is a view of FIG. 5 looking in along the central axis of the duct.

Thus, if the nuclear plant already has a multi-path acoustic flowmeter already installed in one leg, it is only necessary to add a plurality of transducer pairs in the other leg and positioned as illustrated in FIG. 5. Alternatively, if a highly accurate mass flow rate meter could be developed the arrangement of FIG. 5 could be added to both the hot and cold legs to obtain sound velocity indications for implementation of the power computation.

With such arrangement of multiple acoustic paths in the hot leg and multiple acoustic paths in the cold leg, if the corresponding path lengths in one leg are equal to the corresponding path lengths in the other leg, then a common transmitter may simultaneously energize transducers of both legs and instead of two measurements relative to $L/t1$ for each leg, single measurements relative to $\Delta t_{AB}$ may be obtained where $\Delta t_{AB}$ is the difference in arrival times of pulses in one leg relative to pulses in the other leg.

Returning to the present example, all of the quantities necessary for power calculation have been derived, and are implemented in accordance with the following equation:

$$P = \left[ \sum_{i=1}^{n} k_{A_i} \left( \frac{\Delta t_i}{t1_i(t1_i + \Delta t_i)} \right) \right]^x \times$$

$$\left[ k_B \left( \sum_{i=1}^{n} k_{C_i} \left( \frac{1}{t1_i} + \frac{1}{(t1_i + \Delta t_i)} \right) \right) + k_D \right] \times k_F \times$$

$$\left[ \left( \sum_{j=1}^{n} k_{E_j} \left( \frac{1}{t1_j} \right) \right) - \left( \sum_{i=1}^{n} k_{C_i} \left( \frac{1}{t1_i} + \frac{1}{t1_i + \Delta t_i} \right) \right) \right]$$ (21)

where:

$k_{A_i} = W_i L_i^2 \tan \theta_i \frac{D}{2}$ $k_B = \left( \frac{\partial \rho}{\partial C} \right)_P$ $k_{C_i} = \frac{W_i L_i}{2}$ $k_D = \rho c_O$ $k_{E_j} = W_j L_j$ $k_F = \left( \frac{\partial h}{\partial C} \right)_P$ With respect to equation (21), the first term in brackets is the volumetric flow rate Q as determined by the flowmeter and as set out in equation (4). The second term in brackets is the density of the cold leg fluid as set out in equation (7) with the sound velocity as determined by equation (17) with appropriate Gaussian factors. The last term in brackets is simply the sound velocity in the hot leg, from equation (20), minus the sound velocity in the cold leg, as was determined for the density calculation. The difference between these two quantities $C_H$-$C_C$ multiplied by constant $k_F$ is the implementation of equation (10).

Figure 7:
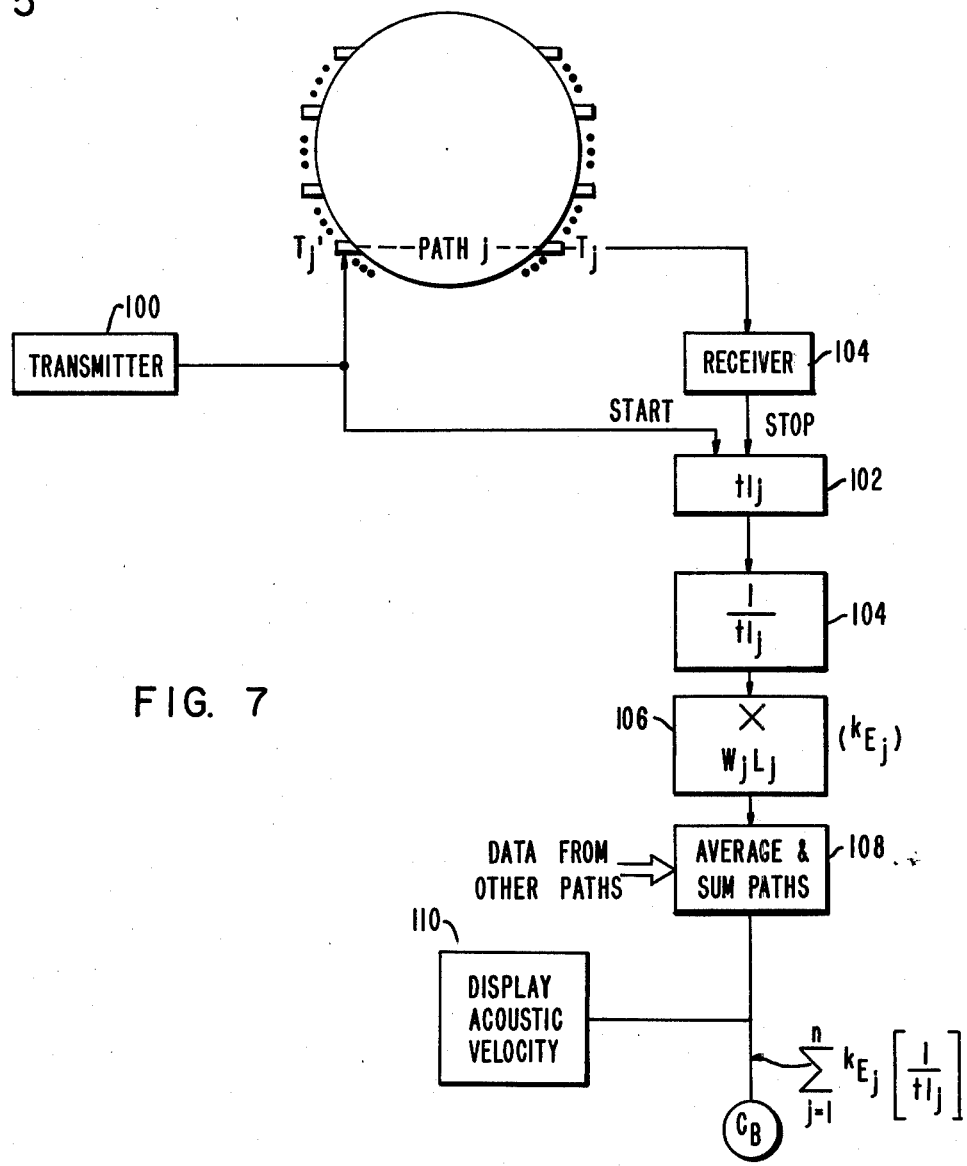
FIG. 7 is a block diagram of electronic circuitry for obtaining sound velocity in the other leg of the loop.
Figure 8:
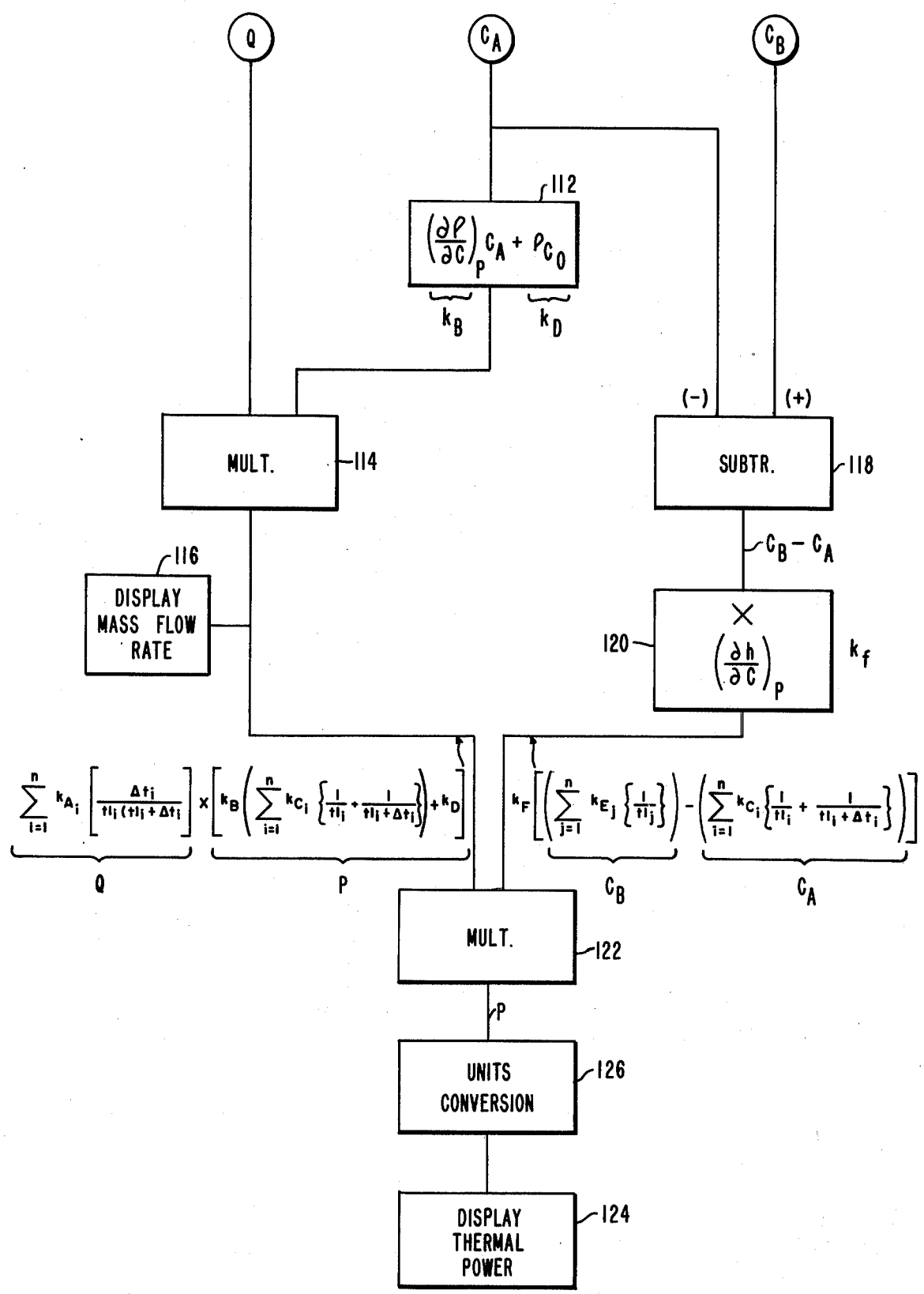
FIG. 8 is a block diagram of electronic circuitry for obtaining an indication of thermal power; and, FIG. 9 is a block diagram of alternate electronic circuitry for obtaining thermal power indications.

FIGS. 6, 7 and 8 illustrate electronic circuitry for implementing the power equation for an n path acoustic flowmeter arrangement in one leg, designated as leg A, and an n path acoustic system for obtaining sound velocity in the other leg, designated as leg B. FIG. 6 illustrates in block diagram form various electronic circuits connected to a path i. A transmitter 70 simultaneously energizes the upstream and downstream transducers of path i so as to project acoustic pulses in opposite directions along the path. Simultaneously therewith, the transmitter starts a t1 counter 72.

The downstream projected pulse arrives first and downstream receiver 74 provides an indication thereof to turn off the t1 counter 72 and to start the $\Delta t$ counter 76. When the upstream projected pulse arrives, upstream receiver 78 will provide an output signal to turn off the $\Delta t$ counter.

Two values are thus obtained, t1 and $\Delta t$, and circuit 80 performs the indicated operation on these two values. The resulting value is multiplied in circuit 82 by the value indicated, which is constant $k_A$ of equation (21) and the results thereof are averaged over a selected time period and summed in circuit 84 with the data from the remaining paths. The output of circuit 84, is therefore the volumetric flow rate Q and is desired its numerical value may be visually outputted on display 86.

From this basic flowmeter arrangement, the sound velocity in leg A may be obtained with the provision of circuit 86, which is responsive to the output from the t1 counter 72 and $\Delta t$ counter 76 for performing the indicated operation with the results being multiplied by the constant indicated in circuit 88, the constant being equivalent to $k_{C_i}$ of equation (21). The output thereof is averaged over a selected time period and summed with the data from the other paths in circuit 90, the output signal of which is sound velocity $C_A$. If desired, a visual indication thereof may be provided on display 92.

The apparatus for obtaining t1 and $\Delta t$ with the subsequent modification of these values to obtain volumetric flow rate is shown functionally in FIG. 6 for one path. Although n duplications (one for each path) of this arrangement are possible, a practical system may use a single transmitter with a single calculating section with different registers for the storage of different constants, with the arrangement being time shared among the paths. One arrangement which may be adapted for such use is illustrated in U.S. Pat. No. 3,918,304 which is hereby incorporated by reference. Additionally, the apparatus for obtaining volumetric flow rate as described is commercially available under the designation LEFM Model 601 sold by Westinghouse Electric Corporation and currently operating in various water treatment plants, hydroelectric plants, pipelines, and nuclear reactor power plants.

The determination of the sound velocity $C_B$ in leg B is accomplished with the arrangement illustrated in FIG. 7 shown for one path, j, of an n path system. Transmitter 100 causes the projection of an acoustic pulse across the duct along path j from transducer $T_j'$ to an opposing transducer $T_j$ and at the same time starts t1 counter 102. When the pulse is received by the opposed transducer $T_j$, receiver 104 will provide an output signal to turn off the t1 counter 102.

Circuit 104 takes the reciprocal of the output of t1 counter 102 and this value is multiplied by the indicated quantity of circuit 106, which quantity is equivalent to $k_{E_j}$ of equation (21). The value thus obtained is averaged over a selected time period and summed with the data from the other paths in circuit 108, the output of which is indicative of the velocity of sound in the fluid in leg B. If desired, a visual output may be provided by display 110.

FIG. 8 illustrates further modification of these quantities Q, $C_A$ and $C_B$ to obtain a value for thermal power. Circuit 112 multiplies the value of $C_A$ by the constant $k_B$ (equivalent to $(\partial \rho/\partial C)_P$) and adds the constant $k_D$ (equivalent to $\rho_{C_O}$). The output of circuit 112 therefore is density $\rho$ which is combined with volumetric flow rate Q in multiplier 114, the output of which is an indication of mass flow rate, which if desired may be visually outputted by means of display 116.

As will be remembered, the mass flow rate is multiplied by the change of enthalpy which in turn is related to the difference in sound velocities in the two legs. Accordingly, the two sound velocities $C_A$ and $C_B$ are operated upon by subtractor 118 and then multiplied, in circuit 120 by the indicated value, equivalent to $k_F$ of equation (21).

The two values, mass flow rate and change of enthalpy are provided to multiplier 122, the output signal of which is indicative of total thermal power which is displayed on unit 124 after any necessary conversion of units in circuit 126.

Figure 9:
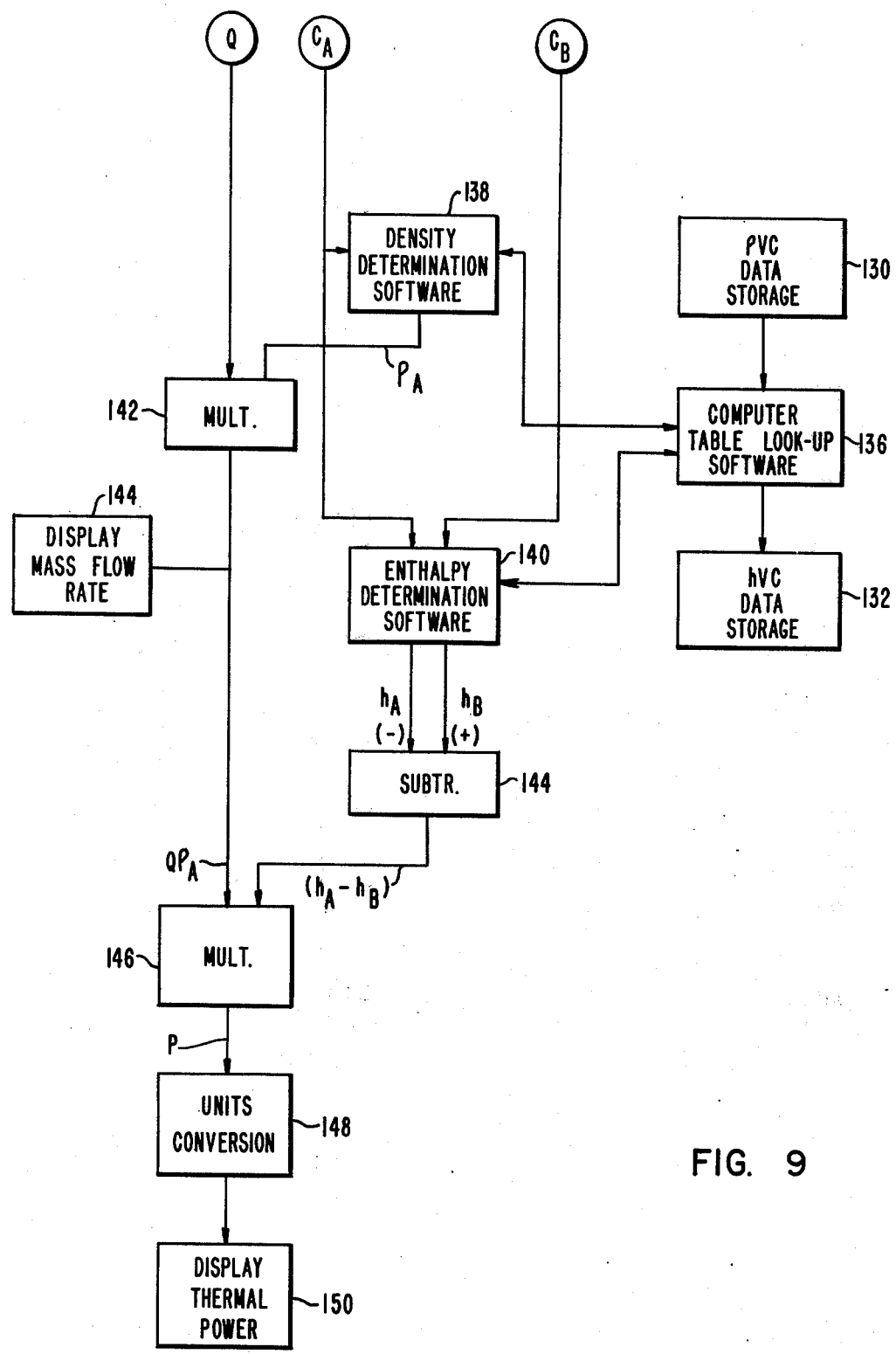

In the computation arrangement just described, the various constants may be stored in separate registers of a computer or read-only memories into which are placed the constant values as dictated by the particular fluid transport system. As an alternative, the thermal power may be determined by the apparatus of FIG. 9 which utilizes data storage sections 130 and 132 for storing respectively the data points of the curve of FIG. 3, density versus sound velocity, and the data points of the curve of FIG. 4, enthalpy versus sound velocity. The apparatus of FIG. 9 may be implemented by a typical digital computer with the storages 130 and 132 being programmable read-only memories or tape or disk storage, by way of example. The computer is programmed such that when $C_A$ and $C_B$ are available, a particular value for $\rho_A$ and the particular values $h_A$ and $h_B$ will be extracted from the respective data storages 130 and 132. This inputting of $C_A$ and $C_B$, table look up, and extraction of particular values is depicted in FIG. 9 by the software blocks 136, 138 and 140.

Multiplier circuitry 142 multiplies the volumetric flow rate by the density to obtain an output indicative of mass flow rate which may if desired, be ouputted on a display 144. The enthalpies for legs A and B are operated upon in subtraction circuit 144 to get the enthalpy difference which is multiplied in circuit 146 by the mass flow rate to provide an output indicative of thermal power. This output, after conversion in unit 148, is provided to display 150.

The computation of thermal power has been described thus far with respect to the primary loop 14 of FIG. 1 wherein an incompressible liquid at a substantially constant pressure is flowing around the loop. In the secondary loop 20, the cold leg 32 conducts a liquid, however, generator 12 provides steam in the hot leg 30.

The secondary loop by itself is also indicative of a single loop system wherein the generator 12 is in fact the heat source for the system and would be by way of example, a fossil fuel burner. Depending upon the apparatus, the steam in hot leg 30 may be saturated steam or superheated steam. For the case of saturated steam, the flow meter apparatus 40 in the cold leg 32 would be identical to that already described, for computing volumetric flow rate Q and sound velocity $C_C$. The apparatus and the computation of thermal power is simplified however by the fact that the enthalpy of the hot leg for the saturated steam system is very nearly a constant and is known for the typical operating range so that acoustic measurements need not be made in the hot leg for enthalpy determination.

For the case of superheated steam, however, the cold leg volumetric flow rate and enthalpy may be determined as previously described, however the hot leg enthalpy must be determined by a measurement of the pressure and temperature of the superheated steam in the hot leg, such as by sensor arrangement 46 of FIG. 1. Apparatus similar to that described in FIG. 9 could then be provided with a data storage of enthalpy as a function of temperature and pressure instead of sound velocity.

Accordingly, there has been described a thermal power measurement apparatus for obtaining an indication of the thermal power generation or consumption of any device using flowing fluid for heat transport. The apparatus utilizes measurements relating to time of flight of acoustic pulses projected across the flowing fluid and with accurate transducer placement, a digital computer and solid state electronics, the error introduced to the power measurements from inaccuracies in time measurement and geometry combine to a maximum value of about 0.67 percent for a single measurement. In actual practice, the measurements will be made many times per second and time average periods on the order of a minute. The time averaging reduces the timing errors to less than 0.1 percent for Q and C. The combination of quadrature integration, thermal gradients, timing and geometry errors and conversion of the measurement to density and enthalpy results in an approximate error for time average power of $\pm\frac{1}{2}$ percent or better.

In the example of a nuclear reactor power plant, only one primary loop was shown. In actuality the plant may include a number of primary loops and thermal power measurements may be obtained for each loop to obtain not only readings and efficiency indications, but thermal power in the individual loops may bge compared to detect any system unbalance.

We claim:

1. Thermal power measuring apparatus for a system having a fluid circulation loop including a heat source and a utilization means and wherein there is a temperature difference between the fluid in an outlet leg from said source to said utilization means and the fluid in an inlet leg from said utilization to said source, the combination comprising:
   (A) acoustic flowmeter means for acoustically obtaining an indication of volumetric flow rate of said fluid in one of said legs;
   (B) means for acoustically obtaining an indication of the speed of sound in said fluid in said one leg;
   (C) means for acoustically obtaining an indication of the speed of sound in said fluid in the other said leg; and
   (D) means for modifying and combining all of said indications to obtain an indication of total thermal power.

2. Apparatus according to claim 1 wherein:
   (A) said acoustic flowmeter means is of the type having a plurality of acoustic measuring paths traversing the fluid under measurement.

3. Apparatus according to claim 2 wherein:
   (A) said acoustic flowmeter means is of the type which periodically projects acoustic pulses in opposite directions along said measuring paths and derives values related to the travel times of said pulses to compute volumetric flow rate.

4. Apparatus according to claim 3 which includes:

(A) circuit means responsive to said derived values related to the travel times of said pulses for determining said indication of the speed of sound in said fluid in said one leg.

5. Apparatus according to claim 3 which includes:
(A) means for obtaining an indication of the density of the fluid in said one leg; and
(B) means for multiplying said density indication times said volumetric flow rate to obtain mass flow rate.

6. Apparatus according to claim 5 wherein:
(A) said density indication is derived utilizing said derived values related to the travel times of said pulses.

7. Apparatus according to claim 1 wherein:
(A) said acoustic flowmeter means is positioned for measuring flow of the fluid in said inlet leg.

8. Apparatus according to claim 1 wherein:
(A) said means for acoustically obtaining an indication of the speed of sound in the fluid in the other leg is of the type which includes a plurality of acoustic measuring paths traversing the fluid under measurement.

9. Apparatus according to claim 8 wherein:
(A) said paths are parallel to one another.

10. Apparatus according to claim 9 wherein:
(A) said paths are perpendicular to the direction of fluid flow.

11. Apparatus according to claim 10 wherein:
(A) each said path includes a transmitting transducer at one end and a receiving transducer at the other end; and
(B) said means is operable to project an acoustic pulse in each path from a respective transmitting transducer to a respective receiving transducer.

12. Apparatus according to claim 11 which includes:
(A) means for determining the time of flight of each said pulse from a transmitting to a receiving transducer; and
(B) means for combining and modifying said times of flight indications to obtain speed of sound in the fluid in said other leg.

13. Apparatus according to claim 12 wherein:
(A) said paths are positioned at predetermined locations relative to a reference; and which includes:
(B) means for obtaining the reciprocal of each said time of flight; and
(C) means for multiplying said reciprocal i) by a predetermined weighting factor dependent upon the path's position relative to said reference and ii) by path length.

14. Thermal power measuring apparatus for a system having a fluid circulation loop including a heat source and a utilization means and wherein there is a temperature difference between the fluid in an outlet leg from said source to said utilization means and the fluid in an inlet leg from said utilization to said source, the combination comprising:
(A) means including acoustic flowmeter means for acoustically obtaining an indication of mass flow rate of said fluid in said inlet leg;
(B) means for acoustically obtaining an indication of the speed of sound in said fluid in said inlet leg;
(C) said fluid in said outlet leg being superheated steam;
(D) means for measuring the pressure and temperature of said superheated steam for determining its enthalpy; and
(E) means for combining said indications with measured pressure and temperature values to obtain an indication of total thermal power.

15. Thermal power measuring apparatus for a system having a fluid circulation loop including a heat source and a utilization means and wherein there is a temperature difference between the fluid in an outlet leg from said source to said utilization means and the fluid in an inlet leg from said utilization to said source, the combination comprising:
(A) means including acoustic flowmeter means for acoustically obtaining an indication of mass flow rate of said fluid in said inlet leg;
(B) means for acoustically obtaining an indication of the speed of sound in said fluid in said inlet leg;
(C) said fluid in said outlet leg being saturated steam having a nearly constant enthalpy value; and
(D) means for combining said indications with said enthalpy value to obtain an indication of total thermal power.

16. A method of obtaining a value for thermal power in a closed loop fluid transport system having a heat source with an outlet leg and an inlet leg, comprising the steps of:
(A) obtaining an indication of the mass flow rate of the fluid in said closed loop;
(B) obtaining an indication of the speed of sound in the fluid in at least one of said legs;
(C) obtaining an indication of the difference in enthalpy between the fluid in said outlet leg and inlet leg utilizing said speed of sound indication; and
(D) combining said mass flow rate and difference in enthalpy indications to obtain an indication of thermal power.

17. A method according to claim 16 wherein:
(A) the fluid in both the inlet and outlet legs is a liquid; and
(B) an indication of the speed of sound in the fluid in both the inlet and outlet legs is obtained and utilized to obtain said difference in enthalpy indication.

18. A method according to claim 16 wherein:
(A) an indication of volumetric flow rate is obtained for the fluid in one of said legs;
(B) an indication of the density of the fluid in said one leg is obtained; and
(C) said volumetric flow rate and density indications are combined to obtain said mass flow rate.

19. A method according to claim 18 wherein:
(A) said indication of the speed of sound is utilized to obtain said density indication.

* * * * *